United States Patent
Baker et al.

(10) Patent No.: US 11,445,983 B2
(45) Date of Patent: Sep. 20, 2022

(54) NON-INVASIVE DETERMINATION OF DISEASE STATES

(71) Applicant: Welch Allyn, Inc., Skaneateles Falls, NY (US)

(72) Inventors: Steven D. Baker, Beaverton, OR (US); Chau Chong Ye, Singapore (MY); Yue Wang, Singapore (MY); Aye Aung, Singapore (MY)

(73) Assignee: Welch Allyn, Inc., Skaneateles Falls, NY (US)

( * ) Notice: Subject to any disclaimer, the term of this patent is extended or adjusted under 35 U.S.C. 154(b) by 156 days.

(21) Appl. No.: 16/803,541

(22) Filed: Feb. 27, 2020

(65) Prior Publication Data

US 2020/0196961 A1    Jun. 25, 2020

Related U.S. Application Data

(62) Division of application No. 15/705,986, filed on Sep. 15, 2017, now Pat. No. 10,624,587.

(Continued)

(51) Int. Cl.
*A61B 5/00* (2006.01)
*A61B 3/11* (2006.01)
(Continued)

(52) U.S. Cl.
CPC .......... *A61B 5/7278* (2013.01); *A61B 3/0025* (2013.01); *A61B 3/112* (2013.01); *A61B 3/14* (2013.01); *A61B 5/02405* (2013.01); *A61B 5/02416* (2013.01); *A61B 5/7282* (2013.01); *A61B 5/0077* (2013.01); *A61B 5/021* (2013.01); *A61B 5/0205* (2013.01); *A61B 5/02444* (2013.01); *A61B 5/0816* (2013.01);
(Continued)

(58) Field of Classification Search
CPC ..................................................... A61B 3/112
See application file for complete search history.

(56) References Cited

U.S. PATENT DOCUMENTS 8,761,853 B2    6/2014   Thaveeprungsriporn et al.
8,977,347 B2    3/2015   Mestha et al.
(Continued)

FOREIGN PATENT DOCUMENTS

EP    2438849 A1    4/2012
WO    2014030091 A1    2/2014
(Continued)

OTHER PUBLICATIONS

Wu, Hao-Yu et al., "Eulerian Video Magnification for Revealing Subtle Changes in the World," http://people.csail.mit.edu/mrub/papers/vidmag.pdf, Jul. 4, 2012, 8 pages.
(Continued)

*Primary Examiner* — Alyssa M Alter
(74) *Attorney, Agent, or Firm* — Merchant & Gould P.C.

(57) ABSTRACT

An example method for estimating a disease state for a patient can include: capturing physiological data including images from the patient over time; processing the physiological data to detect a variability; comparing the variability to a baseline or a range; and estimating the disease state for the patient based upon the comparing of the variability to the baseline or the limit.

10 Claims, 14 Drawing Sheets

Related U.S. Application Data

(60) Provisional application No. 62/440,967, filed on Dec. 30, 2016, provisional application No. 62/395,427, filed on Sep. 16, 2016.

(51) Int. Cl.

| | | |
|---|---|---|
| *A61B 3/14* | (2006.01) | |
| *A61B 3/00* | (2006.01) | |
| *A61B 5/024* | (2006.01) | |
| *A61B 5/0205* | (2006.01) | |
| *A61B 5/08* | (2006.01) | |
| *A61B 5/11* | (2006.01) | |
| *A61B 5/021* | (2006.01) | |
| *A61B 5/107* | (2006.01) | |

(52) U.S. Cl.
CPC ........... *A61B 5/1079* (2013.01); *A61B 5/1107* (2013.01); *A61B 5/1116* (2013.01); *A61B 5/1118* (2013.01); *A61B 5/1128* (2013.01); *A61B 2576/00* (2013.01)

(56) References Cited

U.S. PATENT DOCUMENTS

| | | |
|---|---|---|
| 9,020,185 B2 | 4/2015 | Mestha et al. |
| 2002/0099305 A1* | 7/2002 | Fukushima ............ A61B 5/163 600/558 |
| 2007/0060802 A1 | 3/2007 | Ghevondian et al. |
| 2011/0263952 A1 | 10/2011 | Bergman et al. |
| 2013/0019405 A1 | 1/2013 | Flanagan et al. |
| 2013/0345568 A1 | 12/2013 | Mestha et al. |
| 2014/0275833 A1 | 9/2014 | Vanderpohl, III |
| 2014/0276504 A1 | 9/2014 | Heil et al. |
| 2014/0303454 A1 | 10/2014 | Clifton et al. |
| 2015/0201859 A1 | 7/2015 | Baker et al. |
| 2015/0282724 A1 | 10/2015 | McDuff et al. |
| 2015/0302158 A1 | 10/2015 | Morris et al. |
| 2015/0379370 A1 | 12/2015 | Clifton et al. |
| 2018/0078216 A1 | 3/2018 | Baker et al. |
| 2019/0053707 A1 | 2/2019 | Lane et al. |

FOREIGN PATENT DOCUMENTS

| | | |
|---|---|---|
| WO | 2015078735 A1 | 6/2015 |
| WO | 2015086338 A1 | 6/2015 |
| WO | 2016092290 A1 | 6/2016 |
| WO | 2016-123287 A1 | 8/2016 |

OTHER PUBLICATIONS

Tarassenko, L. et al., "Non-contact vide-based vital sign monitoring using ambient light and auto-regressive models," http://iopscience.iop.org/article/10.1088/0967-3334/35/5/807/meta, Institute of Physics and Engineering in Medicine, 2014, 26 pages.

Chandler, David L., "Your vital signs, on camera," http://news.mit.edu/2010/pulse-camera-1004, Oct. 4, 2010, 3 pages.

International Search Report and Written Opinion in PCT/2018/043052 dated Nov. 6, 2018, 12 pages.

* cited by examiner

NON-INVASIVE DETERMINATION OF DISEASE STATES

BACKGROUND

Various procedures can be used to assess the health state of a patient. These procedures typically involve invasive tactics (e.g., gathering of blood, biopsies, etc.) or, at a minimum, potentially unpleasant processes (e.g., assessment of cardiac performance over time using an ECG machine with multiple leads connected to the patient) in order to determine disease states. Patients sometimes avoid seeking medical treatment because of these unpleasant experiences.

SUMMARY

In one aspect, an example method for estimating a disease state for a patient can include: capturing physiological data including images from the patient over time; processing the physiological data to detect a variability; comparing the variability to a baseline or a range; and estimating the disease state for the patient based upon the comparing of the variability to the baseline or the limit.

DETAILED DESCRIPTION

The present disclosure relates to medical devices that are used to collect physiological data from patients. In the examples described herein, the medical devices use non-invasive methods for assessing various disease states for a patient.

Figure 1:
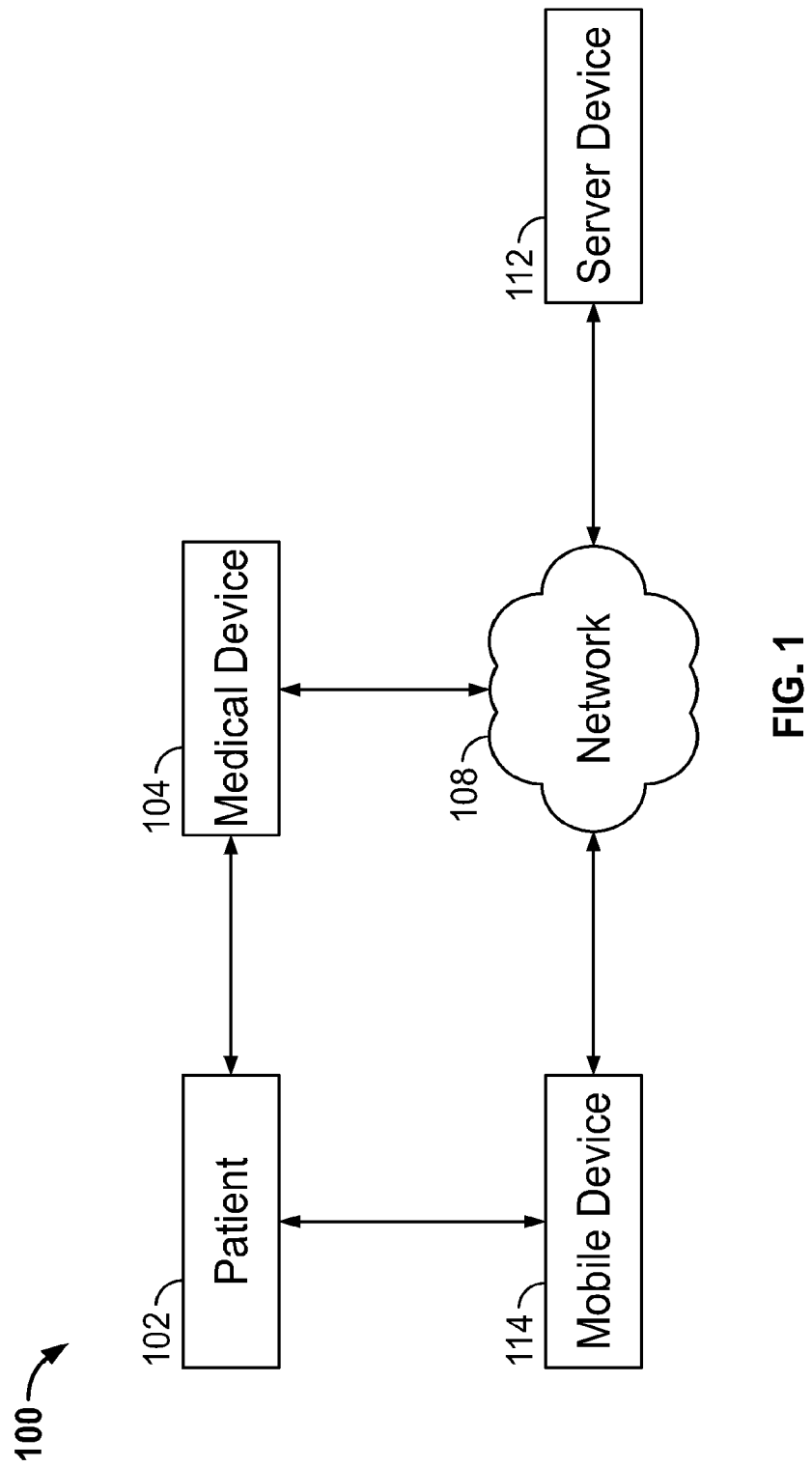
FIG. 1 shows an example system for estimating a disease state of a patient using non-invasive procedures.

FIG. 1 is a block diagram illustrating an example system 100 for assessing the disease state of a patient 102 using non-invasive procedures. Disease includes any condition that causes pain, dysfunction, distress, social problems, or death to the afflicted. This may also include injuries, disabilities, disorders, syndromes, infections, isolated symptoms, deviant behaviors and atypical variations of structure and function.

An example medical device 104 and/or mobile device 114 are used to assess the patient 102 using the non-invasive procedures. The results of the procedures can be analyzed by the medical device 104/mobile device 114 and/or communicated through a network 108 to a server device 112 for analysis and/or storage.

The analysis can result in the assessment of a disease state for the patient 102, including a probability of having or contracting a particular disease. Although only a single patient, medical/mobile device, and server device are shown, the number of each can be increased or decreased as needed to scale the system 100. For example, multiple medical or mobile devices can be used to process multiple patients, and the data from the procedures can be analyzed by a server farm or cloud-based system to provide the disease state assessments.

The medical device 104 can be positioned in a facility, such as a hospital or clinic, at which the patient 102 is located. In another example, the medical device 104 can be located at a facility that is remote geographically from the position of the patient 102 and/or caregiver.

As noted, the medical device 104 communicates with the network 108. In one example, the medical device 104 and the network 108 are part of a CONNEX™ system from Welch Allyn of Skaneateles Falls, N.Y., although other systems can be used. In such an example, the medical devices communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

The network 108 is an electronic communication network that facilitates communication between the medical device 104, the mobile device 114, and the server device 112. An electronic communication network is a set of computing devices and links between the computing devices. The computing devices in the network use the links to enable communication among the computing devices in the network. The network 108 can include routers, switches, mobile access points, bridges, hubs, intrusion detection devices, storage devices, standalone server devices, blade server devices, sensors, desktop computers, firewall devices, laptop computers, handheld computers, mobile telephones, medical devices, and other types of computing devices.

In various embodiments, the network 108 includes various types of links. For example, the network 108 can include wired and/or wireless links. Furthermore, in various embodiments, the network 108 is implemented at various scales. For example, the network 108 can be implemented as one or more local area networks (LANs), metropolitan area networks, subnets, wide area networks (such as the Internet), or can be implemented at another scale, such as a wide area network (WAN), body area network (BAN) and may include Internet of Things (IoT)/Internet of Healthcare (IoH) devices.

In this example, the medical device 104 and the network 108 are all part of the same network. In other words, the medical device 104 and the network 108 communicate with one another over a LAN behind a firewall safeguarding the devices from outside influences on the Internet, such as a firewall. The mobile device 114 may or may not be configured to communicate within the network 108. Alternately, the medical device 104 may communicate via the mobile device 114, for example using a WAN connection available on a cellular phone to reach the network 108. In some instances, the medical device 104 may be instantiated as part of the mobile device 114.

As noted, the medical device 104 can provide various types of functionality, including measuring or monitoring patient physiological parameters. The medical device 104 can include one or more physiological monitor devices configured to measure and possibly display representations of one or more physiological parameters of a patient. In addition, the medical device 104 can include one or more desktop, laptop, or wall-mounted devices. In some embodiments, the medical device 104 is configured to be used by a clinician to monitor the physiological parameters of multiple patients at one time. Such monitor devices are typically not wall mounted.

In this example, the server device 112 is located "in the cloud." In other words, the server device 112 is located outside of the internal network associated with the medical device 104, 104, 105. Typically, the server device 112 does not communicate directly with the medical device 104, but instead communicates with a central server located within the same network as the medical device 104, such as the CONNEX™ system from Welch Allyn of Skaneateles Falls, N.Y. Intermediary servers in the CONNEX™ system, in turn, communicate with the medical device 104. Other configurations are possible.

The medical device 104 and the server device 112 are computing systems. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data.

The mobile device 114 can be any computing device, such as a smartphone, smart watch, tablet, convertible, laptop, etc. that can be used to interact with and capture data from the patient 102. In one example, the mobile device 114 is a smartphone of the patient 102. Similar to that noted above, the mobile device 114 can communicate with the network 108 to provide data captured from the patient 102 to the server device 112.

The mobile device 114 can be programmed to execute one or more applications, such as an application downloaded from the server device 112 and installed on the mobile device 114. These one or more applications can be used to capture data from the patient 102, such as pulse rate, activity level, and/or images of the patient's skin or pupils. The applications can also be programmed to analyze that data, report the data to the server device 112, and/or alert the patient 102 to various indicators, such as possible oncoming disease states. Other configurations are possible. In addition to full-color images, images may be monochromatic and associated with any wavelength, such as images derived from waves received in the range from 3-m to 300 nm. Images may cover any amount of the patient and surrounding area. Unobstructed view is defined to be unobstructed at the wavelength of interest. For example, an instrument operation at 26 GHz would have an unobstructed view through bedding to image chest movement, even though at optical frequencies, the view is obstructed. View to inner ear, retina, etc., may be achieved through optics familiar to those skilled in the art.

Figure 2:
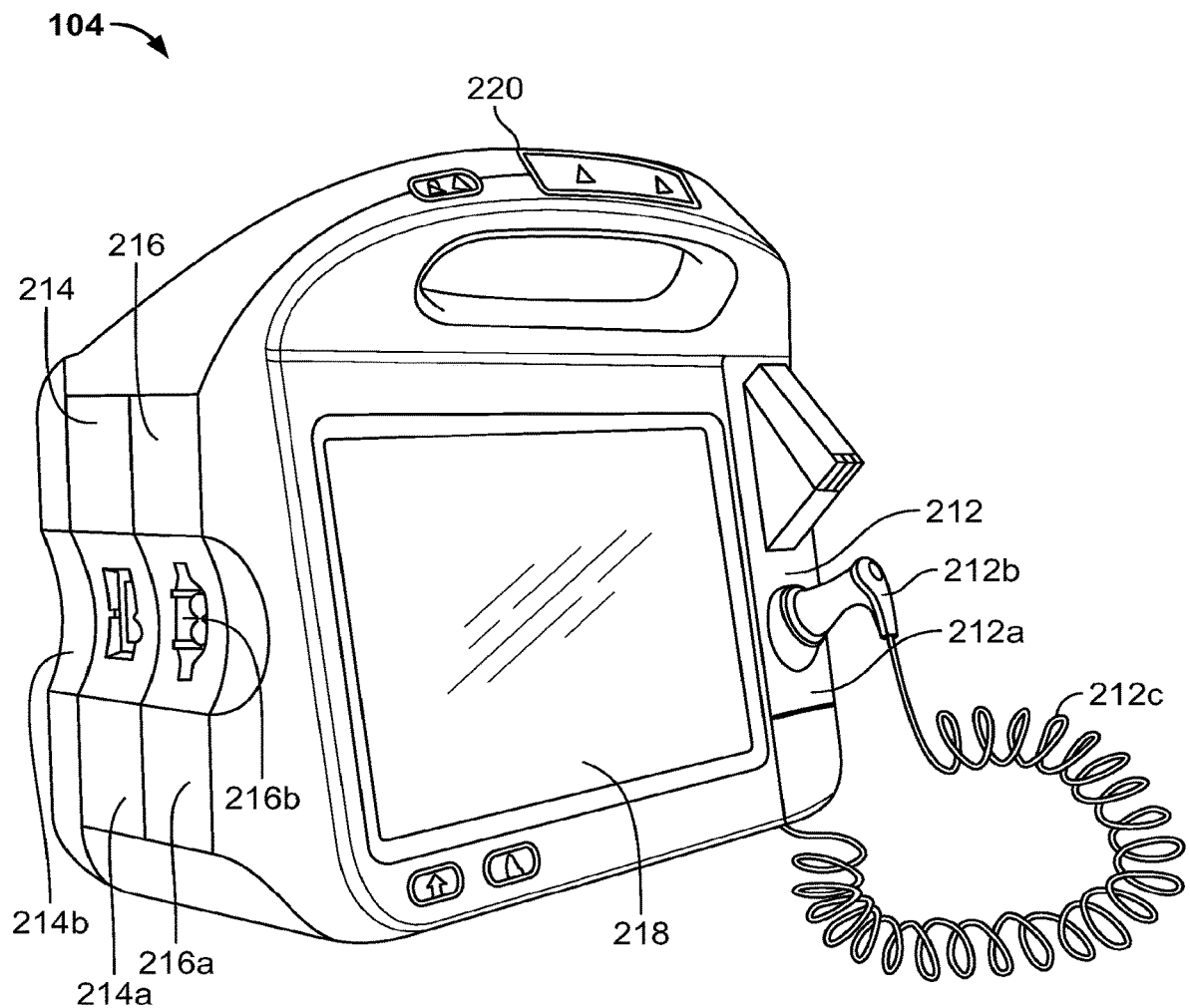
FIG. 2 shows an example medical device of the system of FIG. 1.

FIG. 2 illustrates one example of the medical device 104. The medical device 104 is portable. The medical device 104 includes multiple health care equipment (HCE) modules. Each of the HCE modules is configured to measure one or more physiological parameters of a health-care recipient, also referred to herein as a patient. Other embodiments can include more or fewer components than those shown in FIG. 2, or can include different components that accomplish the same or similar functions.

A temperature measurement module 212 is accessible from the front side of the medical device 104. A SpO2 module 214 and a non-invasive blood pressure (NIBP) module 216 are accessible from a left hand side of the medical device 104. An upper handle portion 220 enables the medical device 104 to be carried by hand.

A front side of the medical device 104 includes a display screen 218 and an outer surface of the temperature measurement module 212. The temperature measurement module 212 is designed to measure the body temperature of a patient. As used in this document, a "module" is a combination of a physical module structure which typically resides within the medical device 104 and optional peripheral components (not shown) that typically attach to and reside outside of the medical device 104.

The temperature measurement module 212 includes a front panel 212a. The front panel 212a has an outer surface that is accessible from the front side of the medical device 104. The front panel 212a provides access to a wall (not shown) storing a removable probe (not shown), also referred to as a temperature probe, that is attached to a probe handle 212b. The probe and its attached probe handle 212b are tethered to the temperature measurement module 212 via an insulated conductor 212c. The probe is designed to make physical contact with a patient in order to sense a body temperature of the patient.

A left hand side of the medical device 104 includes an outer surface of the SpO2 module 214 and an outer surface of the NIBP module 216. The SpO2 module 214 is a HCE module designed to measure oxygen content within the blood of a patient. The NIBP module 216 is a HCE module designed to measure blood pressure of a patient.

As shown, the SpO2 module 214 includes a front panel 214a. The front panel 214a includes an outer surface that is accessible from the left side of the medical device 104. The front panel 214a includes a connector 214b that enables a connection between one or more peripheral SpO2 components (not shown) and a portion of the SpO2 module 214 residing inside the medical device 104. The peripheral SpO2 components reside external to the medical device 104. The peripheral SpO2 components are configured to interoperate with the SpO2 module 214 when connected to the SpO2 module 214 via the connector 214b. In some embodiments, the peripheral SpO2 components include a clip that attaches to an appendage of a patient, such as a finger. The clip is designed to detect and measure a pulse and an oxygen content of blood flowing within the patient.

As shown, the NIBP module 216 includes a front panel 216a having an outer surface that is accessible from the left side of the medical device 104. The front panel 216a includes a connector 216b that enables a connection between one or more peripheral NIBP components (not shown) and a portion of the NIBP module 216 residing inside the medical device 104. The peripheral NIBP components reside external to the medical device 104. The peripheral NIBP components are configured to interoperate with the NIBP module 216 when connected to the NIBP module 216 via the connector 216b. In some embodiments, the peripheral NIBP components include an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

The medical device 104 is able to operate within one or more workflows (or profiles). A workflow is a series of one or more tasks that a user of the medical device 104 performs. When the medical device 104 operates within a workflow, the medical device 104 provides functionality suitable for assisting the user in performing the workflow. When the medical device 104 operates within different workflows, the medical device 104 provides different functionality.

When the medical device 104 is manufactured, the medical device 104 is configured to be able to operate within one or more workflows. After the medical device 104 is manufactured, the medical device 104 can be reconfigured to operate within one or more additional workflows. In this way, a user can adapt the medical device 104 for use in different workflows as needed.

In various embodiments, the medical device 104 operates within various workflows. For example, in some embodiments, the medical device 104 can operate within a monitoring workflow or a non-monitoring workflow. Example types of non-monitoring workflows include, but are not limited to, a spot check workflow, an office workflow, and a triage workflow. A non-limiting example of a monitoring workflow is an intervals workflow.

Figure 3:
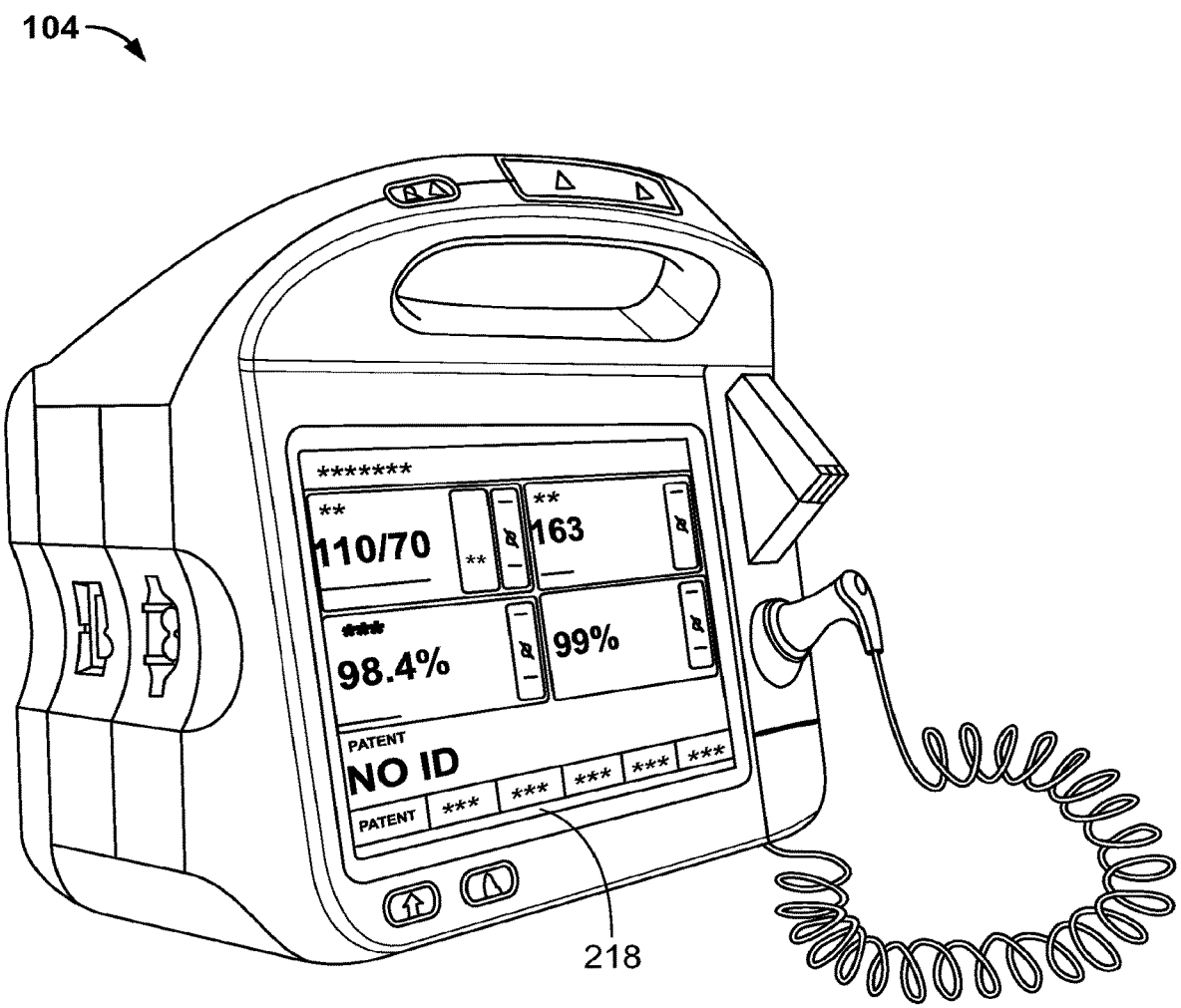
FIG. 3 shows another view of the medical device of FIG. 2.

FIG. 3 illustrates an example user interface displayed on the display screen 218 of FIG. 2. The medical device 104 outputs and displays user interfaces discussed in this document on the display screen 218.

In some examples described herein, the physiological monitor device is a portable device. In other examples, the physiological monitor device is a non-portable device, such as a computing device like a workstation. Many configurations are possible.

The medical device 104 shown in FIGS. 2-3 is only one example of a medical device. All different types of medical devices used to collect patient data can be used.

Figure 4:
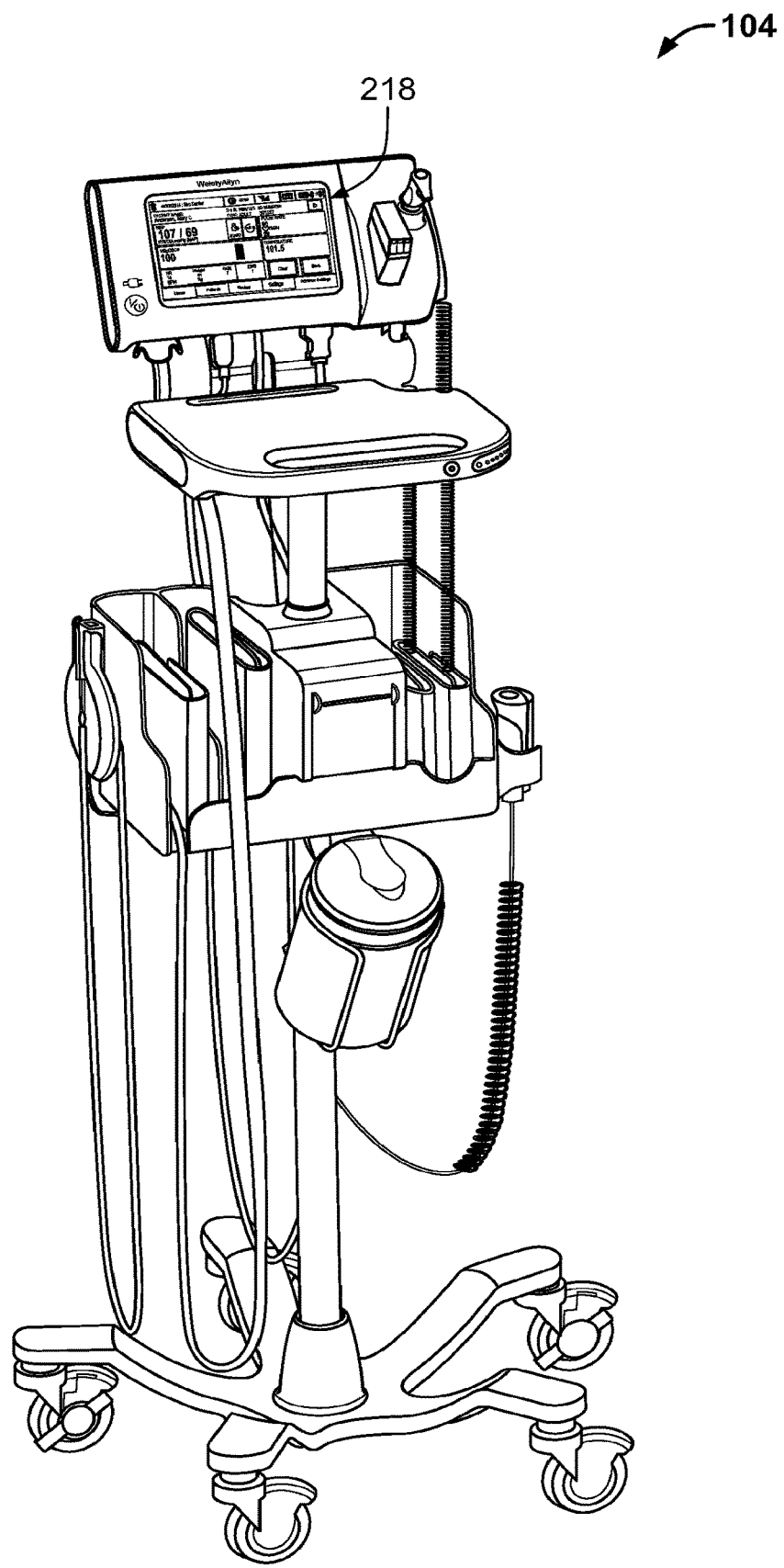
FIG. 4 shows another example medical device of the system of FIG. 1.

For example, another embodiment of the medical device 104 is shown in FIG. 4 on a mobile cart. In some examples, the medical device 104 can be a more compact device that includes a touch screen (e.g., 7 inches) and the ability to execute multiple workflows.

The medical device 104 can be a portable device. In other examples, the medical device 104 can be a stationary device, such as computing devices like workstations. All different types of medical devices used to collect patient data can be used. Many configurations are possible.

Figure 5:
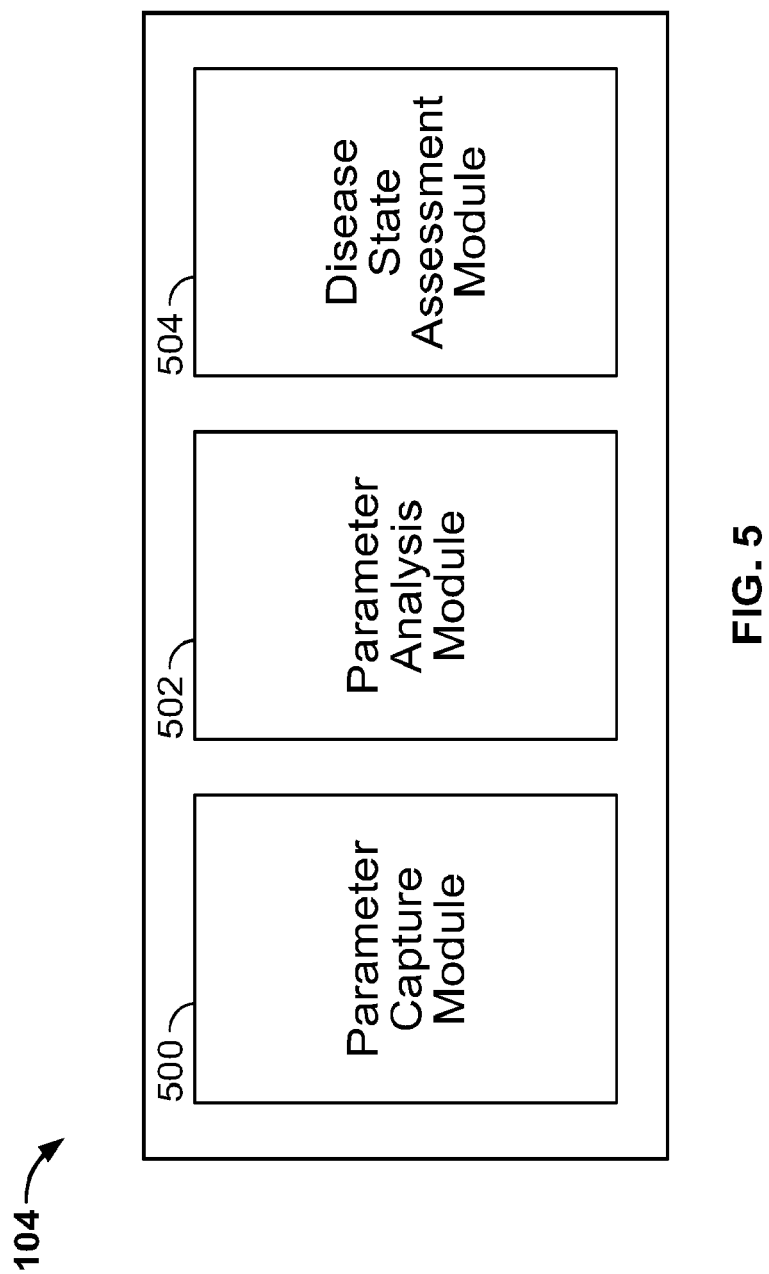
FIG. 5 shows example logical components of the medical device of the system of FIG. 1.

Referring now to FIG. 5, example logical components of the medical device 104 are shown. The medical device 104 is programmed to include a parameter capture module 500, a parameter analysis module 502, and a disease state assessment module 504. The medical device 104 can be programmed to execute one or more of these modules 500, 502, 504 to perform a non-invasive assessment of a disease state of the patient 102, as described further herein. The parameter analysis module 502 and the disease state assessment module 504 may be physically located on a different, external device, e.g., a cloud-based server. In another embodiment, some functions of the parameter analysis module 502 and the disease state assessment module 504 may be present on the medical device 104 and other functions on a remote device. For example, the modules on the medical device 104 might be designed for low processing load, high sensitivity and low selectivity. When the output of these detects a possible disease state, the data are forwarded to the external device for additional analysis that is more selective.

In this example, the medical device 104 includes a parameter capture module 500. In further examples described below, the parameter capture module 500 is programmed to capture one or more parameters associated with the patient 102. In these examples, the parameter capture module 500 captures these parameters in a non-invasive manner.

For example, the parameter capture module 500 can be programmed to capture pulse rate and/or pupil dilation data over time using an imaging device. The first step in analysis is typically creation of a table or plot showing how the pulse rate or pupil diameter changes over time. Details on how this can be accomplished are provided below.

Once the one or more parameters are captured by the parameter capture module 500, the parameter analysis module 502 analyzes the captured data. This analysis can take various forms. For example, the data can be filtered, extrapolated, and compared to baseline data to determine whether changes have occurred.

Once the analysis of the captured data is complete, the disease state assessment module 504 is programmed to estimate a disease state for the patient 102. For example, the disease state assessment module 504 can analyze the comparison of pulse rate variability data to a prior data set and/or to typical data. Typical data may be focused based on patient health factors, and can include: patient's diagnosis, medical history, prescriptions, substance abuse, allergies, genetic data, fluids, and ethnographic background such as age, gender, race and other data that provide a detailed, in-depth description of the patient's everyday life and practice. Typical data depends on the analysis type. For example, for the standard deviation of NN intervals (SDNN), the result is a single number and comparison may be as simple as a Boolean expression. In contrast, a spectrogram is a picture where comparison requires image analysis. The comparison may be a scale where a number or range of numbers is compared to baseline values. For example, a deceleration capacity of less than 2.5 milliseconds indicates a patient with a poor prognosis for cardiac recovery and a deceleration capacity greater than 5 milliseconds indicates a patient with an excellent prognosis. A sliding scale might be used where 2.5-3.75 milliseconds indicates a fair prognosis and 3.75-5 milliseconds indicates a good prognosis. Medical history and ethnography may be entered as parameters into the assessment module 504 or retrieved from an external device, such as cloud server device 112. Medical device 104 and Mobile Device 114 are anticipated to have read/write access to the patient's medical record. Disease state may be assessed in the cloud.

Through annotation of the data with patient outcomes such as morbidity, mortality, length of stay, transfers and other parameters that provide measures of recovery, the data may be used to analyze algorithm performance and provide a way to test new algorithms while minimizing a need for clinical trials. Annotation may be achieved through review of medical records, clinician entry, EMR access or the like.

Figure 6:
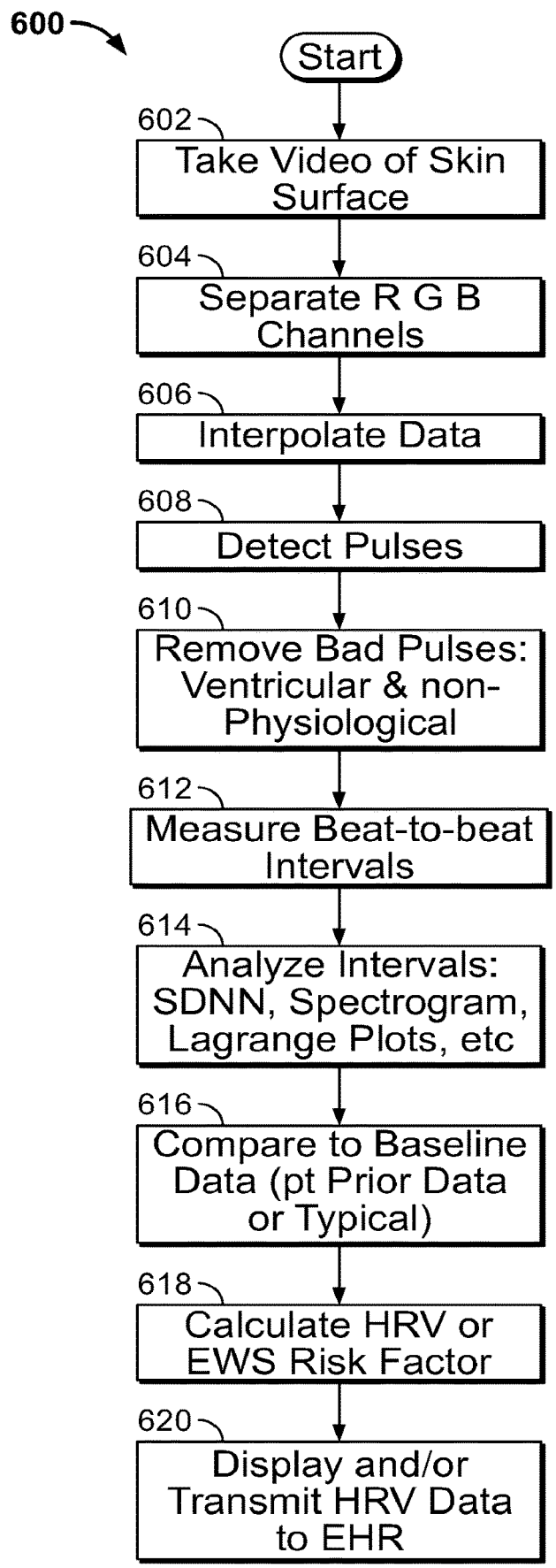
FIG. 6 shows an example method for estimating a disease state of a patient using pulse rate variability.

Referring now to FIG. 6, in one example embodiment, the medical device 104 is configured to estimate a patient's pulse rate variability using non-invasive procedures. In this example, the medical device 104 estimates the pulse rate variability using imaging and an estimated time of the blood volume pulse.

Pulse rate is typically measured in beats per minute. The average duration of time between heart beats is the inverse of the pulse rate. For example, the average duration of time between beats is one second for a pulse rate of sixty beats per minute (i.e., 60 seconds/60 beats). In reality, however, the duration of time between beats is not uniform.

Instead, pulse rate changes continuously in response to the body's ever-changing need for circulation. Pulse rate variability refers to the variation in duration between beats of a person's heart. Within an age group, higher levels of pulse rate variability are typically associated with better health, perhaps indicating that the ability of the autonomic nervous system to respond to internal and external stimuli.

In this embodiment, the medical device 104 is configured (using for example, a camera or other imaging device) to detect pulse rate variability by imaging the skin of the patient 102. In this example, the medical device 104 images the skin at a high frame rate (e.g., 100-200 fps) and uses the captured video/images to detect the patient's heart beat and calculate pulse rate variability. Using a photodetector such as a photodiode illuminated by an LED, for example a 530 nm green LED, allows sampling of the green component of the skin color at sample rates of at least 1 kHz using an SFH 7050 optical sensor from OSRAM Opto Semiconductors of Sunnyvale, Calif. and an AFE4044 integrated analog front end from Texas Instruments of Dallas, Tex.

This information can then be presented to the caregiver in various forms, such as trends, spectrograms, LaGrange plots, histograms, SDNN, root mean square of successive differences (RMSSD), low frequency/high frequency (LF/HF) ratio, pulse rate variability triangular index, triangular interpolation of NN interval (TINN), differential index, logarithmic index, standard deviation of the averages of NN intervals (SDANN), SDNN index, standard deviation of successive differences (SDSD), number of pairs of successive NNs that differ by more than 50 ms (NN50) count, proportion of NN50 divided by total number of NNs (pNN50), total power, very low frequency (VLF power), LF power, HF power, LF/HF ratio, α, etc. Analogous measures may be used for other measures of the parasympathetic nervous system, such as pupil diameter variability. In addition, the estimated pulse rate variability can be further informed using other physiological data from the patient 102, such as oxygen saturation from an SPO2 sensor, from RADAR, from pressure sensors using ballistocardiography, from blood pressure measurements, video analysis and measurement of minute movements in the body due to pulsatile blood flow, video analysis of skin color changes due to pulsatile blood flow, to or any other means by which heart beats or heart beat pulses are detected.

Specifically, the imaging capability of the medical device 104 includes a camera that captures images that can be separated into the Red, Green, Blue (RGB) channels. By separating out the three color components, it is possible to detect the pulse due to each heartbeat. Other color spaces such as HSV may be used. The interval between pulses is measured and then various algorithms are used to analyze the energy content and statistical distribution of beat intervals. Pulse rate variability indices may be stored locally and/or transmitted to an electronic health record. In either case, pulse rate indices may be used as an input to an early warning score, as described further below.

Early warning scores are used to provide more timely assessments and predictions to changes in patient acuity. SAPSII, APACHE, MEWS, PEWS, MEDS, REMS, ASSIST, and SCS are some of the many scoring systems that have been adopted in emergency department (ED), medical/surgical, general care, and ICU environments.

The National Early Warning Score (NEWS) is based on a simple scoring system in which a score is allocated to physiological parameters that are already recorded for patients in general care settings. Six physiological parameters form the basis of the scoring system:
Respiratory rate
Oxygen saturation
Temperature
Systolic blood pressure
Pulse rate
Level of consciousness (AVPU)

BTF is another Early Warning Score program focused on early recognition of patient deterioration. This program builds on operational processes that are in place and is not intended to take clinical assessment away from the nurses. Nursing staff is expected to be able to have access to clinical data and to aggregate and analyze it to form a clinical assessment. To help with this effort, the program established standards outlining what observations should be recorded and what thresholds should trigger a response. Instead of a numbering system, the protocol focuses on human factors and the use of color.

These parameters form the basis of the scoring system:
Respiratory rate
Oxygen saturation
Temperature
Systolic blood pressure
Pulse rate In example embodiments, the medical device 104, mobile device 114, and/or server device 112 are programmed to calculate early warning scores using one or more of the protocols described above. When doing so, the pulse rate variability information can be used to inform and/or modify the early warning score. For example, if the pulse rate variability information indicates a deterioration in the health of the patient 102, the score can be modified as appropriate to indicate this information. Alternately, the early warning score may be based purely on pulse rate variability or on pulse rate variability and a different combination of inputs than existing early warning scoring systems.

The devices 104, 114 also are programmed to communicate those scores, both visually to the caregiver, as well as possibly to a central server, such as server device 112 to be stored in an electronic medical records (EMR) system. Further, the devices 104, 114 are programmed to provide configurable alert messages based upon the calculated early warning scores. Medical device 104 and mobile device 114 are anticipated to have read/write access to the patient's medical record.

Pulse rate variability indices may be used in conjunction with information other than early warning scores. For example, pre-term neonatal patients are susceptible to sepsis. Knowing this, the pulse rate variability for the patient 102 is compared against a baseline for a healthy individual with similar demographics (e.g., neonatal) and, if a significant variance is detected, a warning is provided to the caregiver via the local display of the medical device 104, via the electronic health record system, or a clinical alarm system.

An example method 600 for estimating the pulse rate variability of the patient 102 is shown in FIG. 6. In this example, an image (e.g., video imaging data) is captured of the skin of the patient 102 at operation 602. Next, at operation 604, the imaging data is extracted into the respective RGB channels. Some devices, such as those with HDMI outputs and analog RGB outputs provide RGB as separate channels. In the former case, software written to decode the communication protocol can separate out the various color streams. In the latter case, hardware such as the AD9983A from analog devices may be used to convert analog RGB into digital streams. Color space convertors may be used to convert image processing techniques from one color space to another, such as from as a color space convertor may be used to convert between different color spaces such as, YCbCr, HSV, CMYK, sRGB, Adobe RGB and the like. The system might make a pulse rate analysis using multiple color spaces or might determine which color space provide the optimum results and analyze in that optimum color space.

At operation 606, interpolation is used on the extracted data to determine the peaks of each pulse. The heart beat pulses are detected at operation 608. This can be accomplished by multiple means, e.g., such as using a matched filter that aligns with each pulse to determine a best fit, familiar to those skilled in the art.

At operation 610, the data is smoothed to remove undesired aberrations, such as bad pulses caused by ventricular and non-physiological phenomenon. In one example, pulses have a variability greater than 10 percent are excluded as being aberrant. Pulses determined as pre-ventricular contractions (PVCs) may be separated for a separate analysis.

Figure 8:
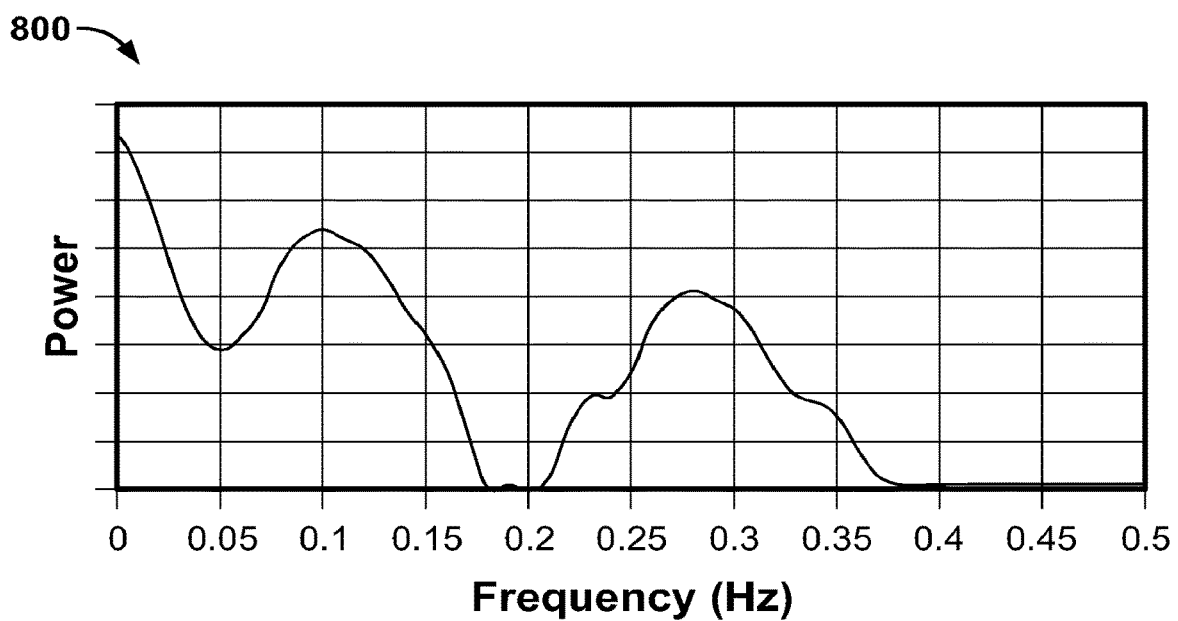
FIG. 8 shows an example power/frequency plot of the pulse rate variability data captured using the method illustrated in FIG. 6.
Figure 9:
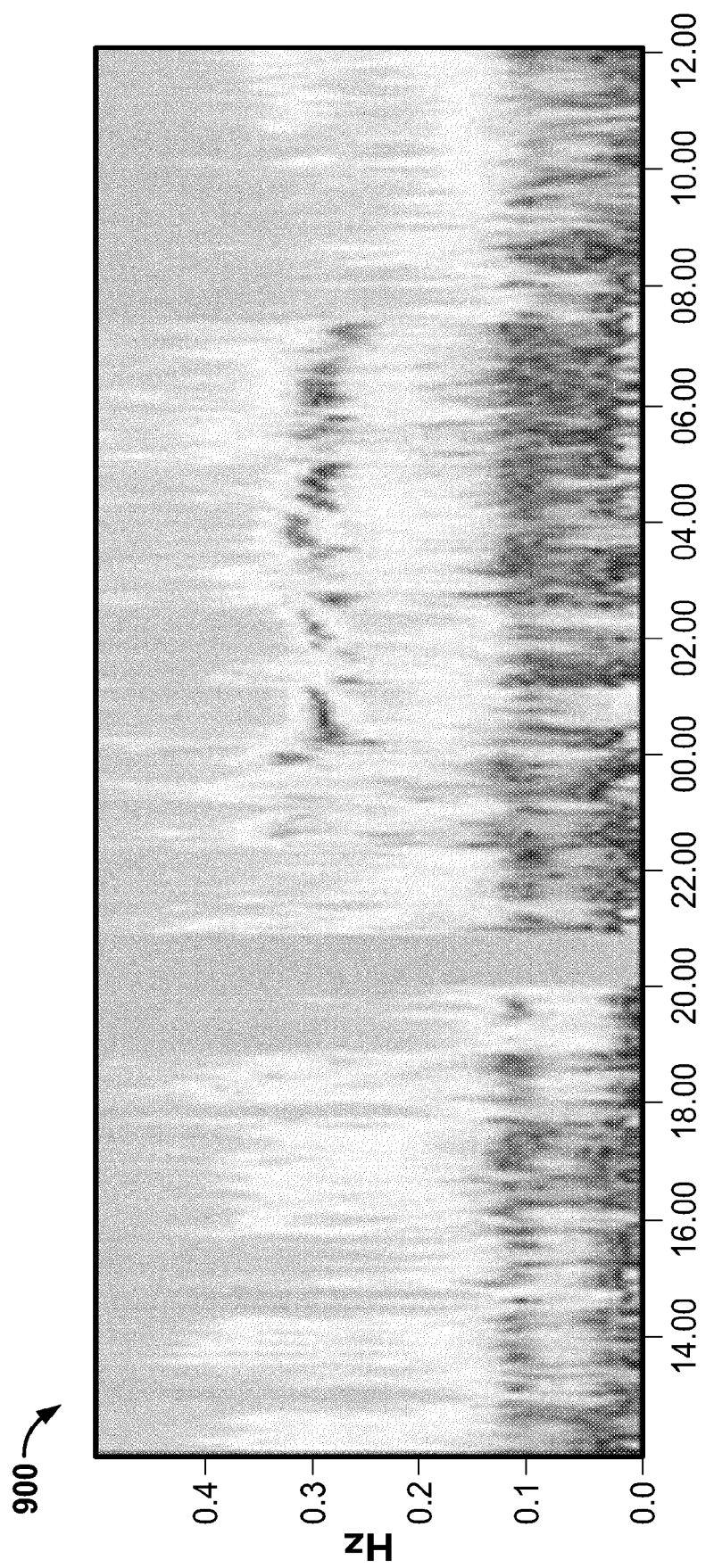
FIG. 9 shows an example spectrogram plot of the pulse rate variability data captured using the method illustrated in FIG. 6.

Next, at operation 612, the beat-to-beat intervals are measured, and these intervals are analyzed at operation 614 using various techniques like SDNN (i.e., the standard deviation of NN interval, calculated for a given period of time), spectrograms (as shown in FIG. 8 and FIG. 9, for example), LaGrange plots, etc. At operation 616, the result is compared to a baseline (either prior data from the patient 102 and/or data for similarly situated individuals). At operation 618, the information is used to calculate an early warning score. Finally, at operation 620, the results are presented to the patient 102 and caregiver and/or saved in the electronic health record.

In yet another example, other schemes are used to detect pulse rate other than visual procedures. For example, microwave and/or ultra-wideband radio technologies can be used to detect pulse rate and thereupon variability. For example, a radar device can be incorporated into the medical device 104. The radar can be used to scan the chest proximal to the heart of the patient 102 and in-phase with the heart beat to optimize detection of the atrial contraction and the ventricular contraction. That is, the beam scans for and detects the location to maximize the atrial response and it scans for and detects the location to maximize the ventricular response.

Then, the system scans the radar beam toward the atria when an atrial contraction is expected and follows it down to the ventricles when a ventricular contraction is expected. The radar beam interacts with the patient and some of the radiated electromagnetic signal is backscattered. This backscattered signal is received by an antenna and the sensor then demodulates data from the transmitted radar signal and tags the data so that it can be correctly associated with the patient 102. This data can thereupon we used to calculate pulse rates and thereupon pulse rate variability. A radar may measure distance by subtracting the pulse reception time from the pulse transmission time, e.g., $\text{distance\_i} = c/(\text{Rx\_time\_i} - \text{Tx\_time\_i})$, where Rx_time_i is the time the system received the $i^{th}$ pulse, Tx_time_is the time the system transmitted the $i^{th}$ pulse, and c is the speed of light. A radar may transmit and receive a series of pulses and measure changes in distance, e.g. $\text{distance\_change} = \text{distance\_i+1} - \text{distance\_i}$. A radar may also compare the phase of the transmitted signal to the phase of the returned signal.

The phase difference, $\sigma$, between the transmitted and received signals is directly proportional to the distance, d, between the radar to the chest. $\sigma = 2*\pi*d/\lambda$, where $\lambda$, is the wavelength of the radar transmission. As the heart beats, the chest cavity presents a small deflection, on the order of 0.1 mm, and this deflection can be detected as a change in the phase difference between the transmitted and received signal. As examples, continuous wave (CW) radar, pulsed radar, chirped radar, pulsed-CW, pulsed-chirped radar may all be used to detect the heartbeat. Detection of motion of the body, as a result of contraction of gross muscles, may be done as a noise-detection-and-elimination step of detecting heart beats. For example, when a patient sits forward, there is a large position change in the chest cavity compared to the sub-millimeter motion from a heartbeat. Detection of motion of the body may be used as a factor for estimating the likelihood that a patient will contract pressure ulcers. Analysis of backscatter at optical wavelengths may also be used to detect heart beat pulses, for example, by examination of video, one can detect minute head movements that are due to pulsatile blood flow and also by examination of video, one can detect color changes in the skin due to pulsatile blood flow.

One may apply multiple measures of pulsatile inputs to improve the system sensitivity and specificity for correctly identifying when a pulse occurs. Backscatter of pressure waves may be used to detect respiration, heart-beat pulses, bladder state (full/empty) and the like. Reduced urine output may be the result of kidney failure, which in turn may be due to sepsis, cholera, dehydration, etc. Pressure ulcers are more likely for patients with soiled sheets; measures of urination and defecation can be factors in the prediction of pressure ulcers. They system may alert a clinician to detection of urination and/or defecation.

Detection of body movement may also be used to detect a patient who may attempt a bed-exit. For example, if the patient sits up and then moves toward the edge of the bed, the system may alert a clinician or modify the bed settings.

Other optical methods may be used, such as a single or small number of photo detectors. The photodetector(s) may use back-scattered background light or light provided by a sensor. The light source may be broadband, e.g., white light, or it may be from a narrow-band optical source, such as a 535 nm green light. The photodetector may be broadband, or filtered to preferentially detect light at the wavelength of a narrow-band optical source.

Figure 7:
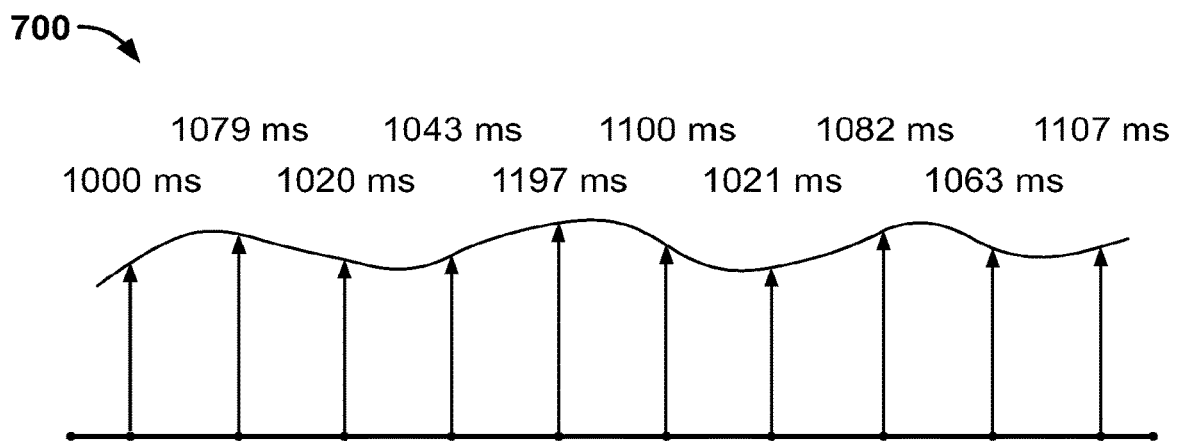
FIG. 7 shows an example graph of pulse rate variability data captured using the method illustrated in FIG. 6.

Referring now to FIGS. 7-9, the medical device 104 and/or the mobile device 114 are configured to illustrate aspects of the pulse rate variability as measured per the method 600. The analysis methods described, including those for producing a spectrogram from pulse rate variability, may be applied to other input sources, such as pupil diameter variability, respiration rate variability, temperature variability, blood pressure variability, and the like.

For pupil diameter variability, a graph similar to that shown in FIG. 7 (for pulse rate variability) can be used, where the units are in millimeters (as opposed to milliseconds for pulse rate variability). For example, the medical device 104 is configured to measure pupil size over time and compare the size to a baseline, either of the patient 102 and/or a similarly situated individual. This can be accomplished using an imaging device (e.g., camera) of the medical device 104 and/or the mobile device 114.

For example, a front facing camera of the mobile device 114 can be programmed to periodically capture images of the pupil(s) as the patient 102 uses the mobile device 114 over time. A pupilometer may also be used. A pupilometer is a medical device that measures the diameter of a pupil, typically in response to external stimulus, such as a light turning on and off. Pupilometers such as the NeuroOptics NPi-200 measure the response time to an externally forced light stimulus and measures size, latency, constriction velocity and dilation velocity. There is no measure of how the pupil diameter varies in response to the autonomic body regulation, such as respiration modulation; however, this could be done as a source of data in this disclosure.

In some examples, the medical device 104 and/or mobile device 114 provide a stimulus (e.g., various lighting configurations and/or video content) to impact the focus and dilation of the pupils. Once captured, the image data can be processed, and a spectrogram of the dilation over time can be created. In the context of the mobile device 114, an application can be executed by the mobile device to periodically stimulate, capture pupil images, and/or analyze/forward the images.

In some examples, a camera with a moderately high frame rate (≥16 fps) and algorithms to track and focus on the eye takes multiple images of the eye and measures the relative change in the pupil diameter over time. The relative size of the pupil matters and other facial features/landmarks such as the overall size of the eye can be used to re-scale if the distance to the camera changes. Images are taken, pupil diameters are measured, and a plot of pupil diameter versus time is created. From this plot, statistics such as mean and standard deviation can be made. Groups of data, for example 128 points, can be transformed into the frequency domain and then put together to create a spectrogram.

As with changes in beat-to-beat interval, the changes in pupil diameter, or pupil diameter variability, are reflective of the state of the autonomic nervous system. These changes can be due to varied factors in addition to ambient light including: increased/decreased attention, surprise, seeing images, hearing sounds, etc. It is noted that the minute changes in pupil diameter are "rich" in healthy patients and relatively plain in unhealthy patients. Respiration modulates the pupil diameter. For example, for a person breathing every 8 seconds, there is an 8-second periodicity in the pupil diameter.

In general terms, the process for calculating the pupil diameter variability involves multiple images of the eye, either using high-speed still image capture or video imaging methods. Each image frame can be verified for quality (e.g., focus, lighting, ability to detect pupil & iris, etc.). The pupil diameter for each eye is measured for each frame. Heuristics are used to discard invalid data, e.g., pupil diameter changes of over 50% from prior reading, pupil size>8 mm, etc. The pupil size detector may use an infrared light and/or infrared detector as a way to increase the contrast of the pupil compared to the iris.

A table of diameter versus sample size can be created. The tabular data may be plotted on a graph similar to the graph 700, as shown in FIG. 7 for pulse rate variability. Further calculations, such as statistics of the data (mean, standard deviation, histogram, etc.) are optionally calculated. Frequency content of the tabular data is calculated, and frequency content can be displayed graphically for a single group (part of all of the tabular data).

For example, FIG. 8 shows power being displayed both in color and in the amplitude on the y-axis of the plot 800. Multiple groups of data from any physiological variability analysis can be displayed to show the trend in frequency over time, as illustrated in the plot 900 of FIG. 9. Power can be compared to a previous baseline or to a general baseline for patients with similar demographics as an indicator of health. Note in the plot 900 three general bands of power at about 0.03, 0.1, and 0.3 Hz that are typical for pulse rate variability. Relative power in different bands can also be compared as indicators of some disease states. Different spectral bands and analysis methods may be used for pupil diameter variability and any other physiological inputs.

Alerts can be provided if the measured attribute (e.g., pulse rate variability, pupil diameter variability, etc.) indicates high probability of health issue, giving the caregiver an indicator that perhaps a more detailed patient assessment is warranted, perhaps including an office visit.

Figure 10:
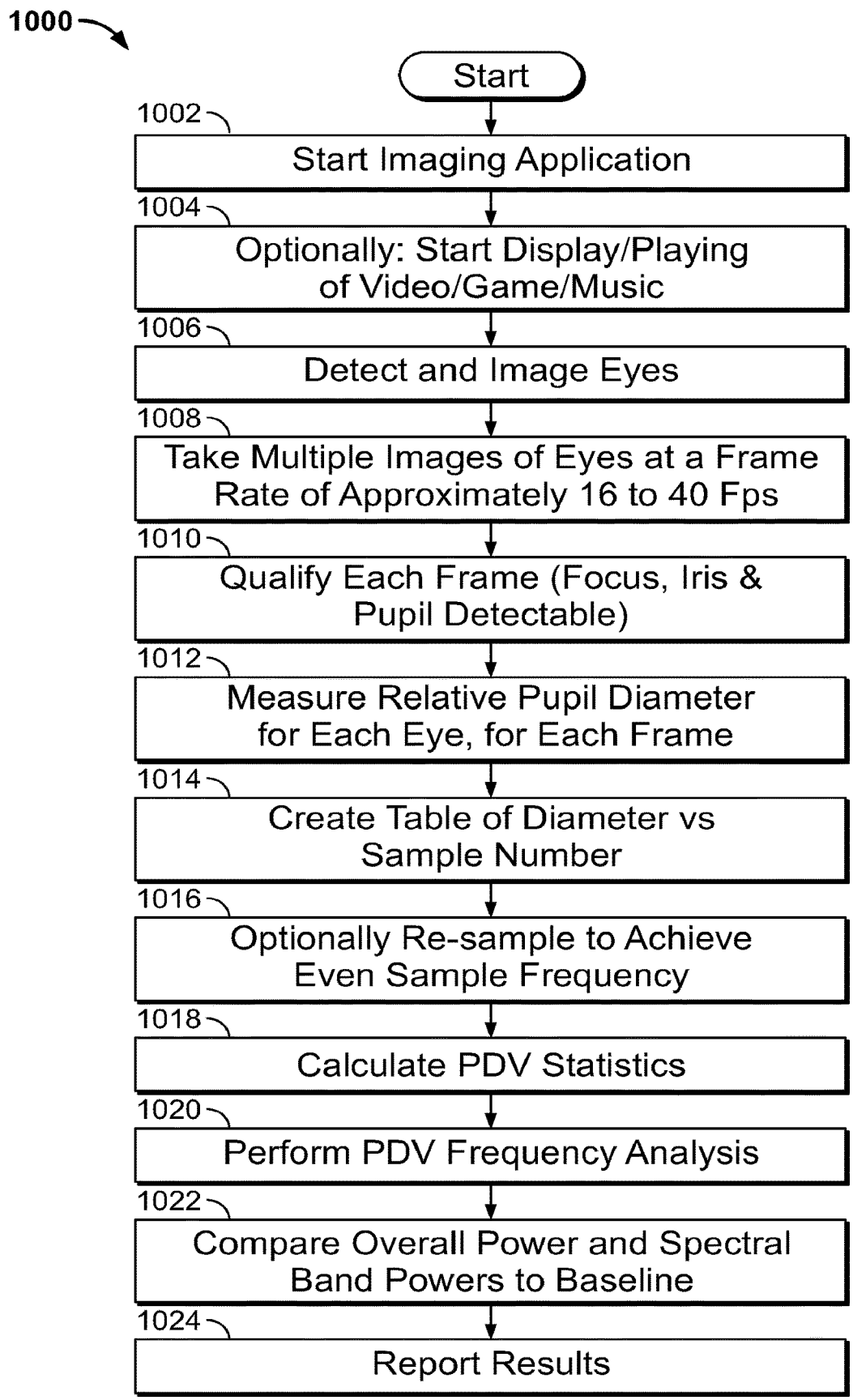
FIG. 10 shows an example method for estimating a disease state of a patient using pupil diameter variability.

Referring now to FIG. 10, an example method 1000 for measuring pupil diameter variability is shown. At operation 1002, imaging is initiated. In the context of a mobile device like a smartphone or tablet, optional operation 1004 can include displaying various images on the mobile device to orient and manipulate the pupil, such as video, video games, etc.

Next, at operation 1006, the pupils of the patient 102 are detected. This can be accomplished, for example, by using one or more automated methods for capturing the pupils of the patient 102. One such method for identifying the pupil is described in U.S. Pat. No. 9,237,846 to Mowrey.

Next, at operation 1008, the one or both pupils are imaged at a given rate, such as at 16 to 40 fps. For a human's typical maximum pupil diameter rate of change, sampling at 40 fps supports a sample for approximately every 0.1 mm of diameter change. Higher frame rates of up to 600 fps would support measurement of diameter changes at a resolution of 0.01 mm at the typical, fastest contraction rates of 6 mm/second. Each image can be qualified at operation 1010, such as for focus, pupil/iris detection, etc. At operation 1012, the relative pupil diameter is measured for each eye for each qualified frame.

Next, at operation 1014, the data is tabulated, such as in a table for each eye. As needed, resampling can be done at operation 1016 depending on the data captured. Next, at operation 1018, various statistics are calculated using the data, and a frequency analysis can be performed at operation 1020 analogous to methods for evaluating pulse rate variability. As with pulse rate variability, the power and spectral bands can be analyzed at operation 1022, such as by using the plots 800 and 900 shown in FIGS. 8 and 9. The results can be presented and/or stored locally or in the electronic health record at operation 1024.

For pulse rate, the sympathetic nervous system increases (accelerates) cardiac activity while the parasympathetic nervous system decreases (decelerates) cardiac activity. In comparison, dilation of the pupil is controlled by the sympathetic nervous system while contraction of the pupil is controlled by the parasympathetic nervous system. As such, analysis of the pupillary dilation/contraction provides a measure of the autonomic nervous system analogous to analysis of increases and decrease in pulse rate.

Figure 11:
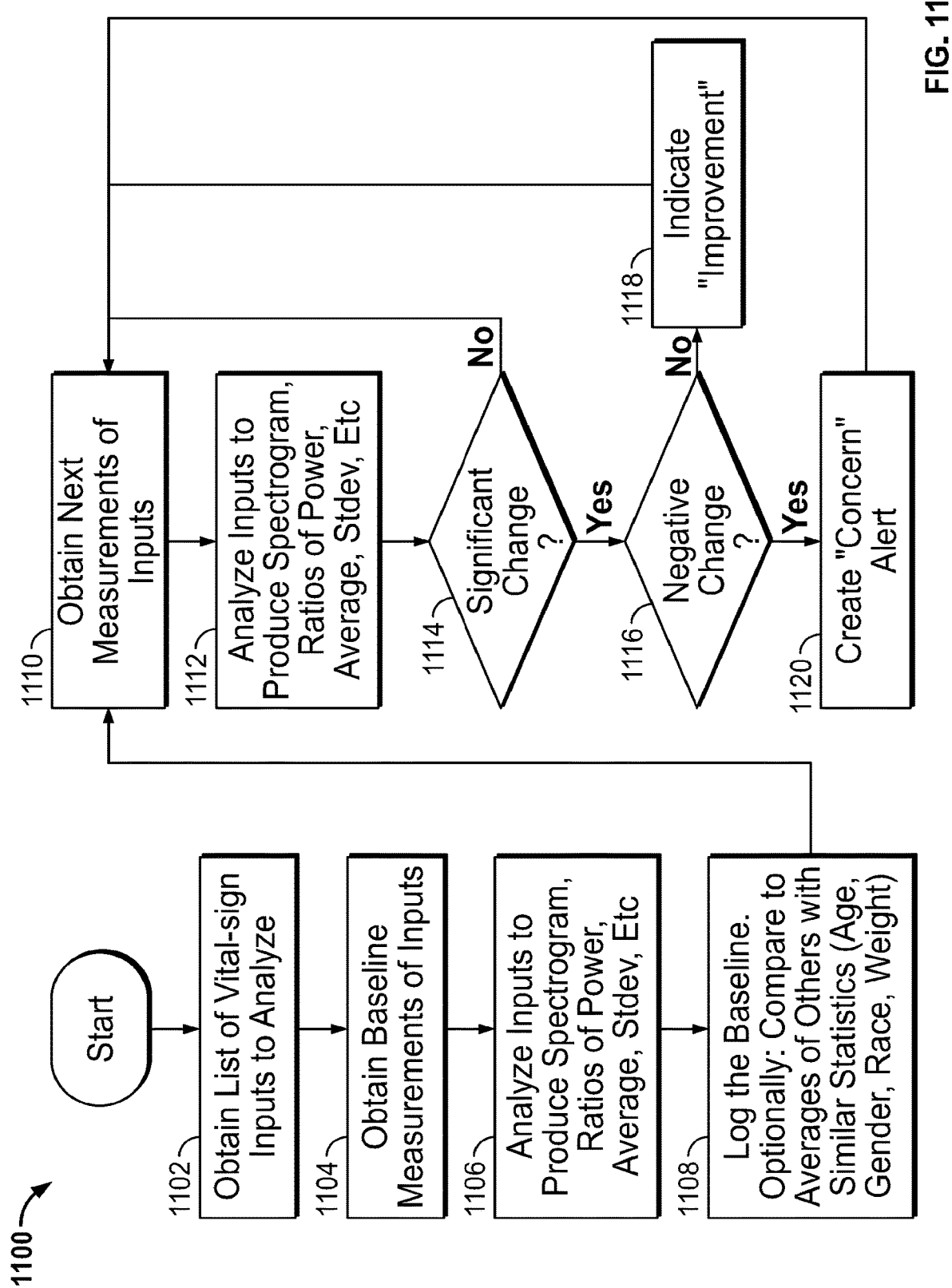
FIG. 11 shows an example method for estimating a disease state of a patient using physiological data captured over time.

Referring now to FIG. 11, as noted, various physiological responses, such as pulse rate and/or pupil diameter variability, can be used over time to predict disease states. Other physiological data, including but not limited to, blood pressure variability, oxygen saturation variability, blood glucose variability, temperature variability, respiration rate variability, respiration depth variability, tympanic membrane motion variability, EEG variability, reflexive response variability, weight variability, urination/bladder-state, defecation, or any measure of variability in chemical content of the blood, urine, saliva or other bodily fluid, can also be used to estimate disease states.

For example, the medical device 104 and/or the mobile device 114 can be used to capture various physiological data of the patient 102 over time. Such data, like the variability of clinical parameters such as pulse rate, respiration rate, SPO2 levels, temperature, pupil response and/or blood pressure can be used as early indicators of disease onset. This data can be collected over time and analyzed to determine variability that indicates a disease state.

As noted, pulse rate variability can be a strong predictor of disease. For example, research shows that pulse rate variability indicators precede the onset of sepsis in adults by several (e.g., typically 1.5) days. A vital-sign variability algorithm can be implemented in a device (e.g., the medical device 104 and/or mobile device 114) that measures a vital sign and provides an alert to the user or health-care worker both when the variability decreases from baseline (indicating diseased state) and when the variability returns to the baseline. Variability may also be used as a health-check for home-health as being tired, stressed, over-exerted decreases the pulse rate variability baseline.

In FIG. 11, an example method 1100 shows how these variabilities can be used to estimate and/or predict disease states for the individual. At operation 1102, vital signs are captured using the medical device 104 and/or the mobile device 114. For example, as noted, physiological information such as pulse rate variability (see FIGS. 6-9) and/or pupil diameter variability (see FIG. 10) can be captured using the camera of the medical device 104/mobile device 114.

Next, at operation 1104, baseline data is obtained. This data can include historic measurements for the patient 102. Or, the baseline data can be obtained from a central repository (e.g., on the server device 112) for an individual who is similarly situated (e.g., same gender, age, race, nationality, geographic origin, diagnosis, etc.).

At operation 1106, a spectrogram and other variability measures are produced based upon the data, such as that shown in FIG. 9. Other statistics can also be used. At operation 1108, the results are compared to the baseline data (either specific to the patient 102 and/or demographic).

Next, at operation 1110, the physiological data is captured over time, and the new data is again analyzed at operation 1112. At operation 1114, significant changes are noted. If no significant changes are noted, control is passed back to operation 1110 for further capture of data. Trends in the changes may be noted and considered as part of the analysis.

If, however, a significant change to the variability is noted, control is instead passed to operation 1116, where a determination is made as to whether the change is positive or negative. If the change is positive, then control is passed to operation 1118 for an optional indication that the disease state is improving, and then control is passed to operation 1110 for further capture of data. If, instead, the change is negative, control is passed to operation 1120, and some type of alert can be generated for the patient 102 and/or the caregiver. Various methods of indicating improvement or decline may be implemented, such as a Likert scale, color coding, audible alerts, and the like.

Figure 12:
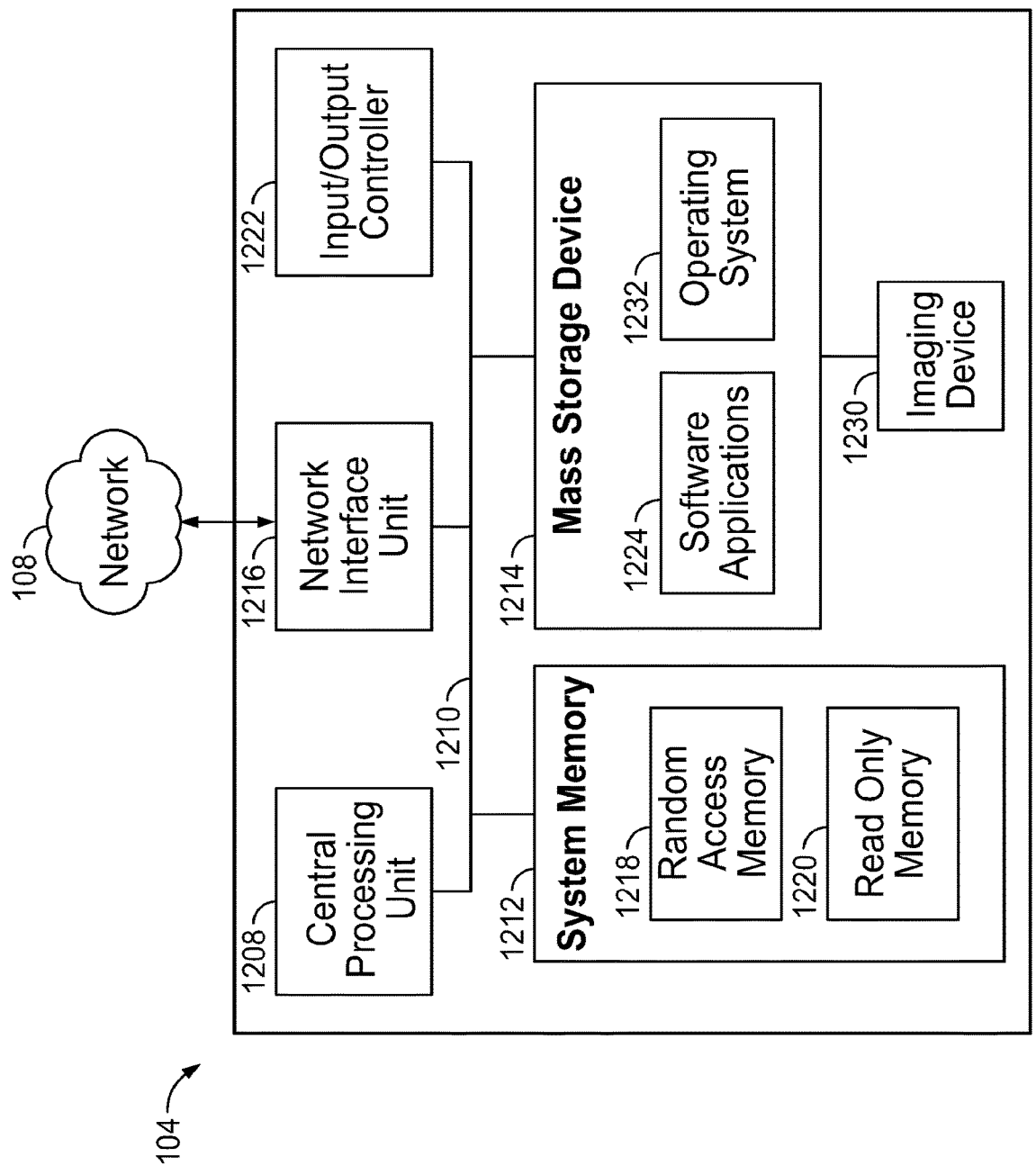
FIG. 12 shows example components of a device of the system of FIG. 1.

FIG. 12 illustrates example physical components of a computing device, such as the medical device 104, server device 112, and/or mobile device 114. As illustrated, the device includes at least one processor or central processing unit ("CPU") 1208, a system memory 1212, and a system bus 1210 that couples the system memory 1212 to the CPU 1208. The system memory 1212 includes a random access memory ("RAM") 1218 and a read-only memory ("ROM") 1220. A basic input/output system containing the basic routines that help to transfer information between elements within the device, such as during startup, is stored in the ROM 1220. The device further includes a mass storage device 1214. The mass storage device 1214 is able to store software instructions and data. The central processing unit 1208 is an example of a processing device.

The mass storage device 1214 is connected to the CPU 1208 through a mass storage controller (not shown) connected to the bus 1210. The mass storage device 1214 and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions. The mass storage device 1214 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

According to various embodiments of the invention, the device may operate in a networked environment using logical connections to remote network devices through the network 108, such as a local network, the Internet, or another type of network. The device connects to the network 108 through a network interface unit 1216 connected to the bus 1210. The network interface unit 1216 may also be utilized to connect to other types of networks and remote computing systems. The device also includes an input/output controller 1222 for receiving and processing input from a number of other devices, including a camera, a keyboard, a mouse, a touch user interface display screen, or another type of input device. Similarly, the input/output controller 1222 may provide output to a touch user interface display screen, a printer, or other type of output device.

The device also includes an imaging device 1230, such as a camera that is configured to capture still or moving images (i.e., video). The camera can be configured to capture high resolution images or video (e.g., 100-200+ fps) that can be used to conduct the analyses described herein.

As mentioned above, the mass storage device 1214 and the RAM 1218 of the device can store software instructions and data. The software instructions include an operating system 1232 suitable for controlling the operation of the device. The mass storage device 1214 and/or the RAM 1218 also store software instructions, that when executed by the CPU 1208, cause the device to provide the functionality of the device discussed in this document. For example, the mass storage device 1214 and/or the RAM 1218 can store software instructions that, when executed by the CPU 1208, cause the medical and/or mobile device to capture images and determine variability of one or more physiological measurements.

Figure 13:
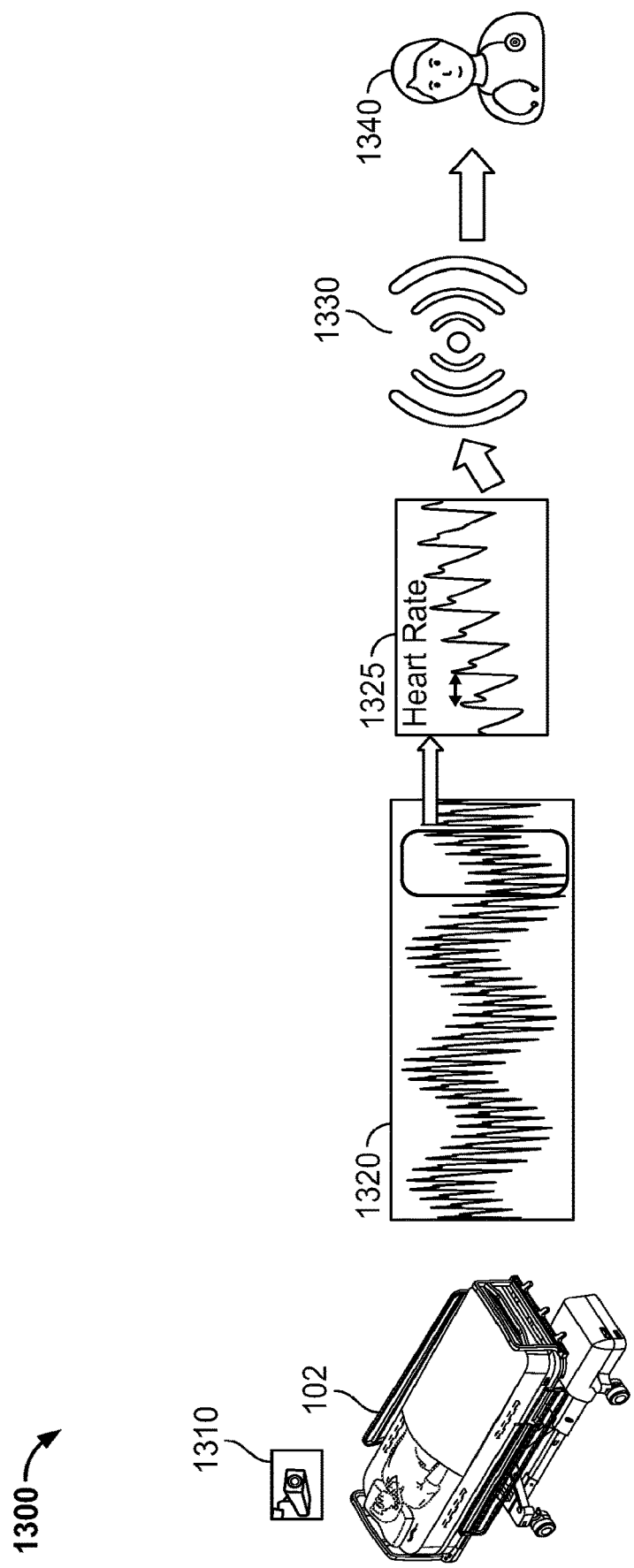
FIG. 13 shows another example system for estimating vital signs from facial images.
Figure 14:
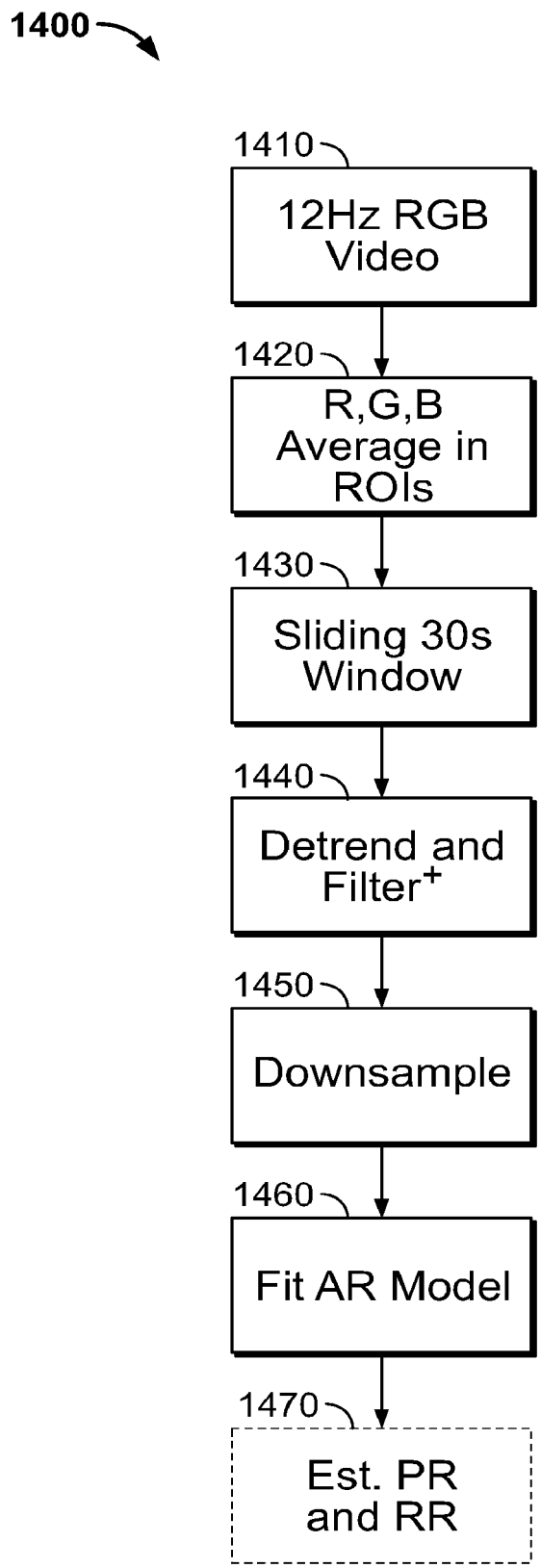
FIG. 14 shows an example method for estimating pulse rate and/or respiratory rate from video using the system of FIG. 13.
Figure 15:
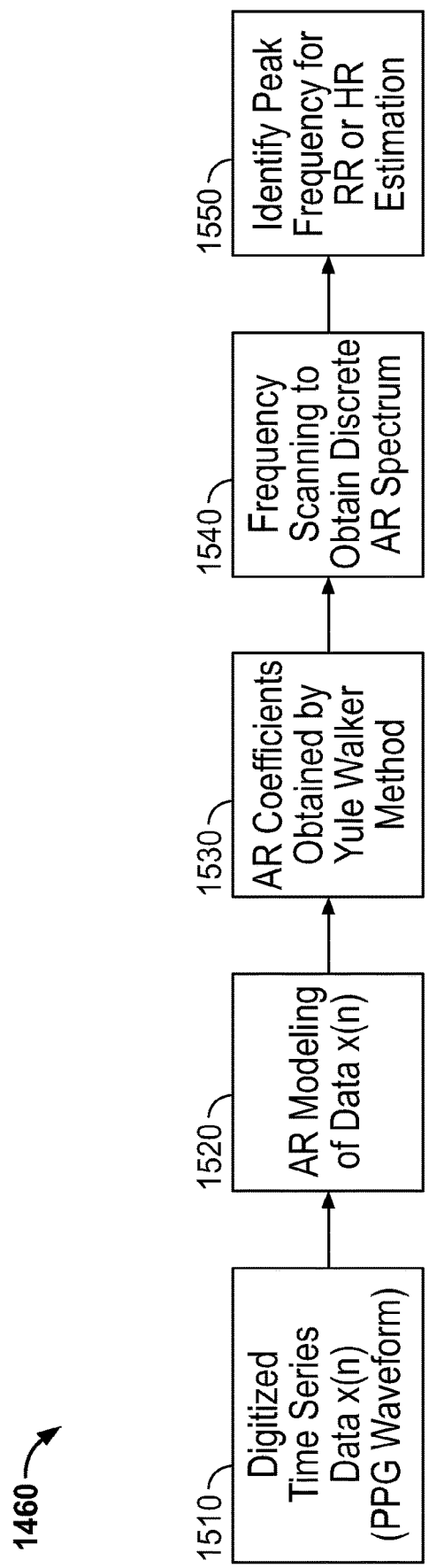
FIG. 15 shows additional example details on the application of an autoregressive model from the method of FIG. 14.

Referring now to FIGS. 13-15, another embodiment of a system is illustrated for estimating vital signs, like blood volume changes associated with the cardiac cycle, from facial images of human subjects. Patients' vital signs, like pulse rate and respiratory rate, can be monitored continuously by caregivers, which can be useful for patients suffering respiratory disorder diseases and heart problems. This example provides a low-cost and non-contact solution for patients who have a difficulty using contact and wearable devices.

In this example shown in FIG. 13, a system 1300 includes a camera 1310 that is placed to capture a sequence of images of the patient 102. The images are segmented into various regions (e.g., face, upper body and background). The camera 1310 may be a still camera that acquires images at suitable frame rate (e.g., 10-16 images per second) or a video camera.

Subtle changes in pixel values of the facial region (e.g., forehead and cheek) are used to estimate pulse rate 1325, as depicted in the waveform 1320. In addition, low frequency amplitude variation of the camera reflectance signal can be used for estimating respiratory rate. The pulse and/or respiratory rates can be estimated and recorded continuously. If abnormal rates are detected, an alert 1330 is triggered and sent to a caregiver 1340 in order to take proper action, if needed. The trends of pulse and respiratory rates will also be available for the caregiver 1340 to analyze. The system may use combine multiple analysis methods, such as the changes in pixel values and the minute motions of the head occur with each pulse to achieve a higher fidelity system than one that uses just one of the methods.

Referring now to FIG. 14, an example method 1400 for estimating pulse rate and/or respiratory rate from video is shown. In this example, the video is captured at operation 1410 as a 12 Hz RBG video feed, although other configurations can be used.

Next at operation 1420, the captured video feed is broken into red, green, and blue components and an average region of interest (ROI) is calculated. At operation 1430, a sliding window of a defined size (e.g., a 30 second window in this example) is used to analyze the data.

At operation 1440, the data is filtered (e.g., detrended and filtered). The filtering can be altered depending on the desired data, such as different filtering for pulse rate and respiratory rate.

Next, at operation 1450, the data can be downsampled. At operation 1460, an autoregressive (AR) model is applied, as described further below. Finally, at operation 1470, an estimate of pulse rate and/or respiratory rate are provided. This estimate can be captured over time to provide trending for the caregiver. In addition, acute alerting can be provided if significant changes are captured.

Referring now to FIG. 15, additional details on the application of the AR model in operation 1460 of the method 1400 for spectrum estimation of pulse rate and/or respiratory rate are provided.

Generally, in this example, the time series of data collected by the camera is digitized at operation 1510 to form a photoplethysmogram (PPG) waveform. Next, the data is modeled to form the AR model at operation 1520.

At operation 1530, the AR coefficients are calculated using an equation such as the Yule-Walker equations. Next, at operation 1540, frequency scanning is used to obtain the discrete AR spectrum. Finally, at operation 1550, the peak frequency for pulse rate or respiratory rate is estimated.

More specifically, the AR model of the digitized time series data (PPG waveform) can be expressed as follows.

$$x(n) + \sum_{i=1}^{m} a_i x(n-i) = e(n)$$

where m is the order of the AR process, $\{a_i\}_{i=1}^{m}$ represents the AR coefficients, e(n) is assumed to be the white noise with zero mean and variance $\sigma^2$. In the domain of the z-transform, the transfer function H(z) relating the output to the input can be written as follows.

$$H(z) = \frac{1}{A(z)} \text{ where } A(z) = \sum_{k=0}^{m} a_k z^{-k}$$

and $z^{-1}$ is the unit delay operator, that is, $z^{-k}x(n)=x(n-k)$. Then, the power spectral density (PSD) of the AR model can be expressed as follows.

$$P(\omega) = \sigma^2 \left|\frac{1}{A(\omega)}\right|^2 \text{ where } A(\omega) = \sum_{k=0}^{m} a_k e^{-jk\omega},$$

and A(ω) is obtained by substituting $z=e^{j\omega}$ in A(z). As noted, the AR coefficients can be obtained by the Yule-Walker equations.

After obtaining the AR coefficients, the frequency scanning process can be performed to find the peak frequency locations for a range of frequencies of interest. As such, the AR frequency spectrum is obtained in order to estimate the frequency components of the given digitized time series data. The frequency f of each peak can be obtained from the angular frequency ω=2πf. Measurements over time may be presented to the clinician through various means including display of current data and/or trends on the medical device 104, mobile device 114, or via server device 112, which allows clinicians to view medical data via an EHR interface.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method for estimating a disease state for a patient, the method comprising:
   detecting a pupil of the patient;
   capturing images of the pupil over time;
   processing the images to estimate a pupil diameter variability; and
   creating a spectrogram of the pupil diameter variability over time.

2. The method of claim 1, further comprising:
   comparing the pupil diameter variability to a baseline; and
   estimating the disease state for the patient based upon the comparing of the pupil diameter variability to the baseline.

3. The method of claim 2, further comprising issuing an alert when the estimated disease state indicates a high probability of a health issue of the patient.

4. The method of claim 1, further comprising transmitting the pupil diameter variability to an electronic medical record.

5. The method of claim 1, further comprising annotating data with at least one patient outcome metric.

6. The method of claim 5, further comprising using one or more annotations of the data to measure an algorithm performance.

7. The method of claim 1, wherein processing the images to estimate the pupil diameter variability comprises measuring pupil size with an infrared detector.

8. The method of claim 1, further comprising measuring a diameter of the pupil with a pupilometer.

9. The method of claim 1, wherein the images of the pupil are captured with a high-speed still image camera or video camera.

10. The method of claim 1, wherein the images of the pupil are captured at a rate of from 16 to 600 frames per second.

* * * * *